United States Patent [19]

Nielsen

[11] Patent Number: Plant 7,540

[45] Date of Patent: Jun. 4, 1991

[54] NEW MINIATURE ROSE PLANT NAMED RUINIELOV

[75] Inventor: Ove Nielsen, Broby, Denmark

[73] Assignee: DeRuiter's Nieuwe Rozen B.V., Netherlands

[21] Appl. No.: 410,545

[22] Filed: Sep. 21, 1989

[51] Int. Cl.[5] ..... A01H 5/00

[52] U.S. Cl. ..... Plt./10

[58] Field of Search ..... Plt. 7, 10

*Primary Examiner*—Howard J. Locker

*Attorney, Agent, or Firm*—Christie, Parker & Hale

[57] ABSTRACT

A new variety of miniature rose having dark red flowers produced on a good pot forcing plant.

1 Drawing Sheet

SUMMARY OF THE INVENTION

The present invention relates to a new and distinct variety of rose plant of the miniature rose class, which was discovered by me as a natural mutation in a controlled planting of the rose known as "Ruimired", U.S. Plant Pat. No. 5,770, the disclosure of which is incorporated herein by reference. The new variety differs from "Ruimired" in flower coloring. The variety denomination of this new rose is "Ruinielov".

Among the novel characteristics possessed by this new variety which distinguishes it from its parents and all other varieties of which I am aware are its attractive dark red flowers borne on a plant suitable for production of flowering pot plants and that can be reproduced through propagation by cutting or by grafting. Flowers of the new variety are long lasting on the plant. Asexual reproduction by budding and by grafting of the new variety as performed in Broby, Denmark, shows that the foregoing and other distinguishing characteristics come true to form and are established and transmitted through succeeding propagation.

The accompanying drawing shows typical specimens of the vegetative growth and flowers of the new variety in different stages of development depicted in color as nearly true as it is reasonably possible to make the same in a color illustration of this character.

BRIEF DESCRIPTION OF THE DRAWING

The photo illustration shows details of the new variety of miniature rose.

DESCRIPTION OF PREFERRED EMBODIMENT

The following is a detailed description of my new variety, with color terminology in accordance with The Royal Horticultural Society Color Chart (R.H.S.C.C.) and horticultural terminology in accordance with standard terminology used in UPOV-approved horticultural guidelines. The terminology used in color description herein refers to plate numbers in the aforementioned color chart.

Parentage: Mutation (sport) of the rose variety known as "Ruimired".
Class: Miniature.

As can be seen in the accompanying illustration, "Ruinielov" is exemplified by attractive dark red flowers which open well and which are complimented by dark green foliage. Since flowering is nearly continuous, the floriferous "Ruinielov" pot plant can remain attractively in bloom for long periods when given proper care and culture.

The photo shows details of the new variety "Ruinielov". In the illustration there is shown the top of a young shoot 1; compound three, five and seven leaflet leaves, 2, 3, and 4; a side branch, 5, with thorns; a green bud, 6, showing color and a bud, 7, with slightly more sepal separation; and open blooms, 8, and 9. Also shown are flower stems 10, 11 and 12 with sepals and reproductive organs.

The following further horticultural observations were made of specimens grown outdoor in Holland.

FLOWER

Blooming habit: Nearly continuous.

A. Bud:
- (1) *Size.*—Medium.
- (2) *Form.*—Pointed, circular.
- (3) *Color.*—As sepals divide, bud color is near 46A.
- (4) *Sepals.*—Longer than bud, slight to extensive foliation, medium sepal extension.
- (5) *Penduncle.*—Length — medium. Aspect — straight. Strength — erect. Color — medium green.

B. Bloom:

*Flower.*—Average size for miniature; viewed from top — irregularly rounded; viewed from side: (A) upper part of fully opened flower — flattened convex; (B) lower part of fully opened flower —convex.
- (1) *Size.*—Average size when fully expanded — about 3.5 to 4 cm.
- (2) *Borne.*—Primarily singly, one to a stem.
- (3) *Form.*—Ovoid at first, becoming flat; outer petals reflex and roll under.
- (4) *Petalage.*—Many petaled, fully double.
- (5) *Color.*—After sepals fall and petals unfurl, predominant flower color is near 45A, B to 46A. Color through this range is substantially stable, occasional white streak. Petals at flower centers may approach 47B. Petals toward point of petal attachment, near 155A.

C. Petals:
- (1) *Texture.*—Medium to thick.
- (2) *Appearance.*—Inside velvety and outside satiny.
- (3) *Form.*—Obovate.
- (4) *Arrangement.*—Regularly arranged, imbricated.
- (5) *Petaloids in center.*—Few.
- (6) *Persistence.*—Drop off cleanly.

(7) *Fragrance.*—Slight to none.
(8) *Lasting Quality.*—Long lasting quality on plant.

REPRODUCTIVE ORGANS

A. Stamens, filaments and anthers:
*Arrangement and color.*—Styles —medium length, yellow green; color — filaments pale yellow.
B. Pollen:
*Color.*—Yellow orange.
C. Styles: Even, medium length, bunched.
D. Stigma: Full, extend above anthers.
E. Hips: Small, funnel-shaped.

PLANT

A. Form: Upright to bushy.
B. Growth: Vigorous.
C. Foliage: Compound 3, 5 and 7 leaflets.
(1) *Size.*—Small to medium for a miniature.
(2) *Quantity.*—Abundant.
(3) *Color.*—Foliage at time of first flowering — dark green.
(4) *Shape.*—Oval, pointed.
(5) *Texture.*—Upper side is medium glossy; under side is matte.
(6) *Edge.*—Serrate.
(7) *Serration.*—Ordinary, acuminate apices.

(8) *Leaf stem.*—Color — medium green.
(9) *Stipules.*—Medium length, slightly bearded, light green, distinct auricle.
(10) *Leaflet.*—Cross section — concave; terminal leaflet — short, narrow, obtuse base; petiole — short.
D. Wood:
(1) *New wood.*—Color — purple.
(2) *Old wood.*—Color — medium green.
E. Prickles (thorns):
(1) *Prickles.*—Present, quantity (main stalk) — ordinary; form — straight and slanted downward; shape of upper side — deep concave; shape of lower side — deep concave; length — medium number $\leqq 5$ mm; very few $<5$ mm; color — tan to pale pink; position — irregular.
(2) *Bristles and glandular hairs.*—Few to none.
F. Winter hardiness: Needs protection outdoors in severe climates.

I claim:

1. A new and distinct variety of rose plant of the miniature rose class, substantially as shown and described, characterized particularly by a plant suitable for growing in pots and by attractive dark red flowers which are long lasting on the plant.

* * * * *

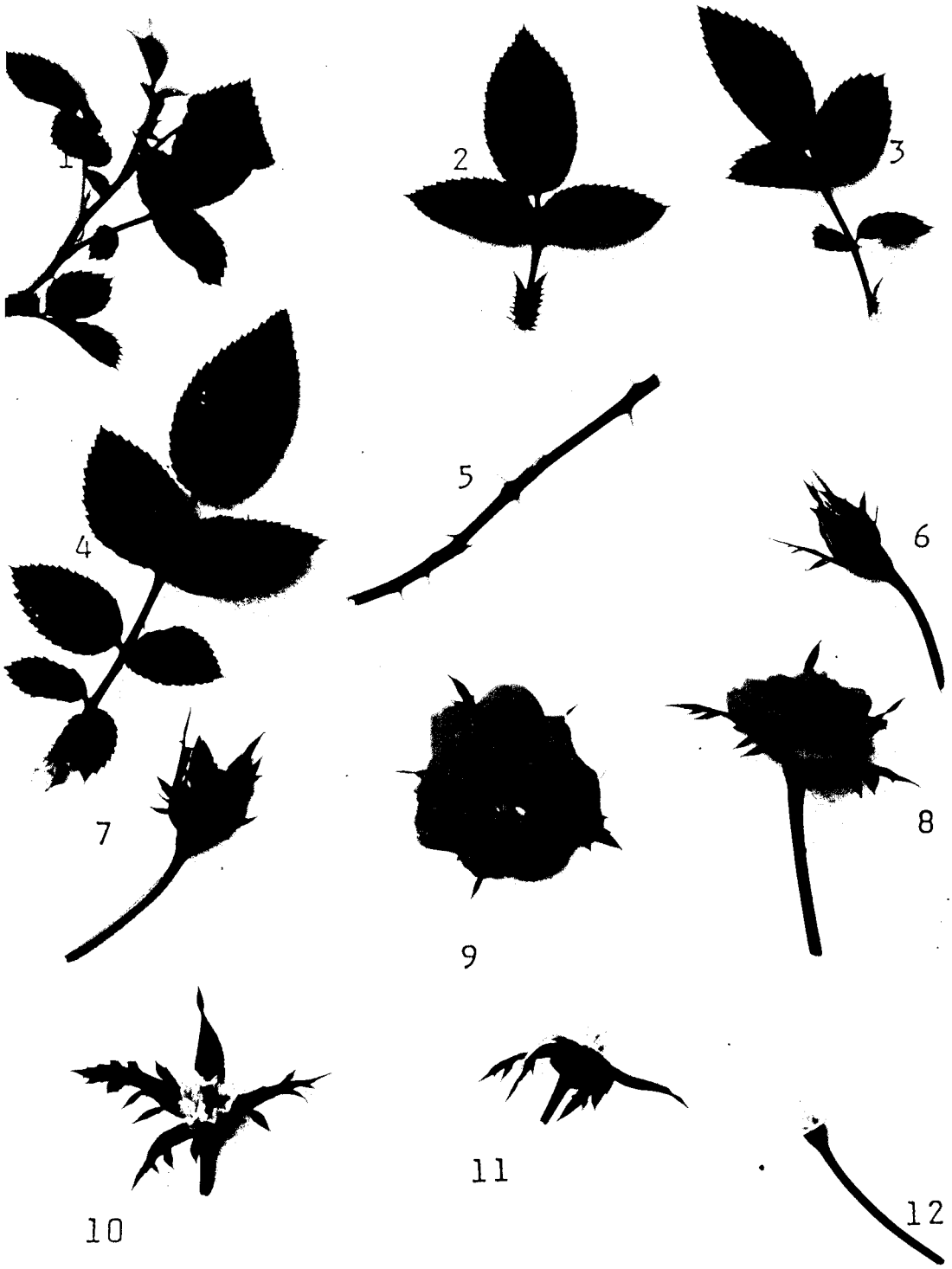
RUINIELOV
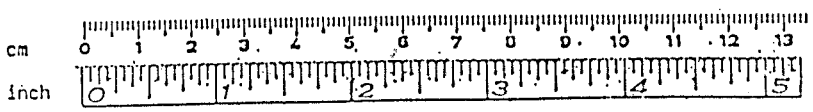

UNITED STATES PATENT AND TRADEMARK OFFICE

CERTIFICATE OF CORRECTION

PATENT NO. : PP 7,540

DATED : June 4, 1991

INVENTOR(S) : Ove Nielsen

It is certified that error appears in the above-identified patent and that said Letters Patent is hereby corrected as shown below:

Column 1, line 16, change "cutting" to --cuttings--.

Column 4, line 15, after "few" change "<5 mm" to -->5 mm--.

Signed and Sealed this

Twenty-third Day of March, 1993

*Attest:*

STEPHEN G. KUNIN

*Attesting Officer*

*Acting Commissioner of Patents and Trademarks*